United States Patent
Chang et al.

(10) Patent No.: US 11,964,926 B2
(45) Date of Patent: *Apr. 23, 2024

(54) IONIC LIQUID ALKYLATION OF ISOBUTANE WITH ETHYLENE TO PRODUCE ALKYLATE

(71) Applicant: CHEVRON U.S.A. INC., San Ramon, CA (US)

(72) Inventors: Bong-Kyu Chang, Novato, CA (US); Hye-Kyung Cho Timken, Albany, CA (US); Huping Luo, Moraga, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/954,420

(22) Filed: Sep. 28, 2022

(65) Prior Publication Data

US 2023/0183151 A1 Jun. 15, 2023

Related U.S. Application Data

(60) Provisional application No. 63/289,685, filed on Dec. 15, 2021.

(51) Int. Cl.
| | |
|---|---|
| *C07C 2/60* | (2006.01) |
| *B01J 31/02* | (2006.01) |
| *C07C 9/16* | (2006.01) |
| *C10L 1/06* | (2006.01) |

(52) U.S. Cl.
CPC .............. *C07C 2/60* (2013.01); *B01J 31/0244* (2013.01); *C07C 9/16* (2013.01); *C10L 1/06* (2013.01); *C07C 2531/02* (2013.01); *C10L 2200/0423* (2013.01); *C10L 2270/023* (2013.01)

(58) Field of Classification Search
CPC ......... C07C 2/60; C07C 9/16; C07C 2531/02; B01J 31/0244; C10L 1/06; C10L 2200/0423; C10L 2270/023
USPC .................................................. 585/16
See application file for complete search history.

(56) References Cited

U.S. PATENT DOCUMENTS

| | | | |
|---|---|---|---|
| 3,800,001 | A | 3/1974 | Prescott et al. |
| 3,873,635 | A | 3/1975 | Prescott et al. |
| 7,432,409 | B2 | 10/2008 | Elomari et al. |
| 9,079,815 | B2 | 7/2015 | Mukherjee et al. |
| 11,643,373 | B1 * | 5/2023 | Luo ..................... C07C 2/60 585/708 |

(Continued)

FOREIGN PATENT DOCUMENTS

| | | |
|---|---|---|
| WO | 2007112238 A2 | 10/2007 |
| WO | 2009085446 A1 | 7/2009 |

OTHER PUBLICATIONS

J-M. Goupil, J-L. Poirier and D. Cornet "Alkylation of Isobutane by Ethylene: A Thermodynamic Study" Ind. Eng. Chem. Res. 1994, 33, 712-717.

(Continued)

*Primary Examiner* — Prem C Singh
*Assistant Examiner* — Francis C Campanell
(74) *Attorney, Agent, or Firm* — Merchant & Gould P.C.

(57) ABSTRACT

A process for producing high octane alkylate is provided. The process involves reacting isobutane and ethylene using an ionic liquid catalyst. Reaction conditions can be chosen to assist in attaining, or to optimize, desirable alkylate yields and/or properties.

18 Claims, 2 Drawing Sheets

(56) References Cited

U.S. PATENT DOCUMENTS

2006/0135839 A1\* 6/2006 Elomari ............... C10G 29/205
                                                                            585/709

OTHER PUBLICATIONS

PCT International Search Report, International application No. PCT/IB2022/059227, mailed Jan. 13, 2023.

\* cited by examiner

IONIC LIQUID ALKYLATION OF ISOBUTANE WITH ETHYLENE TO PRODUCE ALKYLATE

CROSS-REFERENCE OF RELATED APPLICATIONS

This application claims the priority benefit of U.S. Provisional Patent Application No. 63/289,685, filed Dec. 15, 2021, the disclosure of which is incorporated herein by reference.

FIELD

This present disclosure relates a process for isoparaffin-olefin alkylation. More specifically, the present disclosure relates to a process for producing a high octane alkylate by reacting isobutane with ethylene in the presence of an acidic ionic liquid catalyst.

BACKGROUND

Because of its clean-fuel properties (e.g., high octane rating, low-vapor pressure, and low sulfur content), alkylate is considered one of the most desired components in the gasoline pool. As demand for cleaner-burning fuel has increased, refiners are relying more than ever on alkylate to meet stringent gasoline specifications. With increasing pressure to reduce motor vehicle exhaust emissions, alkylate is well-positioned to be in steady demand for decades to come.

Most alkylate is produced in refineries by a process known as isoparaffin alkylation. Commercially, isoparaffin alkylation is an acid catalyzed reaction that combines C3-C5 light olefins from a fluid catalytic cracking (FCC) unit with isobutane to produce a relatively high octane branched-chain paraffinic hydrocarbon fuel, including iso-heptane and iso-octane. Predominant alkylation technologies utilized by refiners require a liquid acid catalyst such as sulfuric acid ($H_2SO_4$) or hydrofluoric acid (HF).

Ethylene is another major component produced in the FCC unit. However, the direct alkylation of ethylene has not been possible with conventional liquid acid alkylation catalysts (e.g., $H_2SO_4$, HF) and processes due to the relatively slow kinetics of the reaction. Efforts to produce alkylate from ethylene have relied on dimerizing ethylene to butylene in a dimerization process unit, followed by alkylation with isobutane in the alkylation process unit. This method requires significant extra capital investment for the dimerization unit. In addition, alkylate yield per barrel of ethylene is very low.

Therefore, there is a need for an improved process for alkylation of light olefins.

SUMMARY

In one aspect, there is provided an alkylation process comprising: passing an isobutane feed and an ethylene feed to an alkylation reactor, wherein the alkylation reactor contains an ionic liquid catalyst, the ionic liquid catalyst comprising an organic cation and a halometallate anion, for reacting the isobutane and ethylene to generate an alkylate having a research octane number (RON) of 93 or more; wherein the alkylation reactor is operated at reaction conditions including a temperature of from 30° C. to 100° C., a pressure of from 300 psig to 700 psig (2068 kPa to 4826 kPa), an overall paraffin to olefin molar ratio from 2 to 20, and a residence time of from 5 minutes to 1 hour.

In another aspect, there is provided an alkylate having a research octane number (RON) of 93 or more, comprising: (i) at least 70 wt. % C6 paraffins, wherein the C6 paraffins comprise isomers of dimethylbutane (DMB) and methylpentane (MP) and a molar ratio of DMB to MP is at least 7:1; (ii) 30 wt. % or less C8 paraffins; and (iii) less than 20 wt. % C9+ paraffins.

DETAILED DESCRIPTION

Definitions

Figure 1:
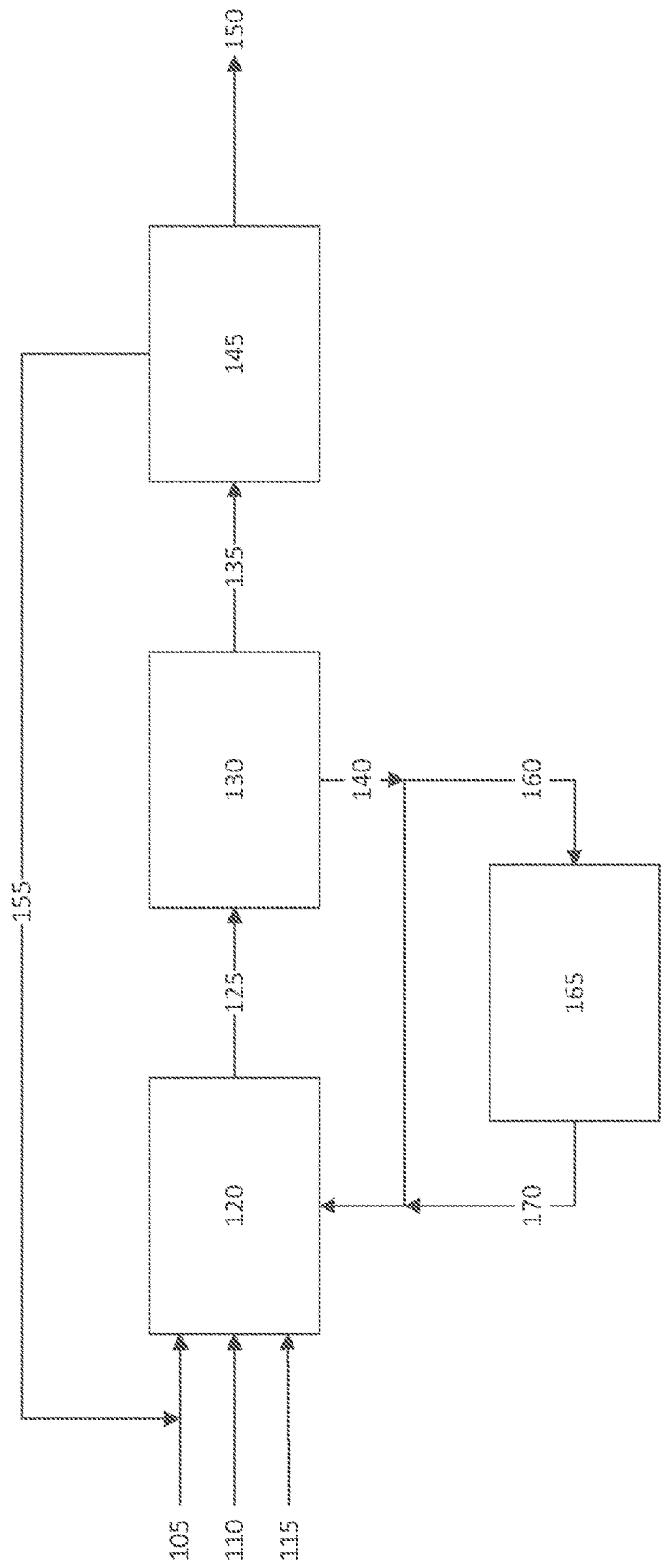
FIG. 1 is an illustration of one embodiment of an alkylation process of the present disclosure.

The term "alkylate" means the reaction products generated in alkylation reactions between an olefin and an isoparaffin in the presence of a catalyst. Alkylates typically are highly branched paraffinic hydrocarbons. Refiners can use alkylate as a gasoline blend stock to boost octane, reduce Reid vapor pressure (RVP), and reduce olefin content in a final gasoline blend.

The term "Cn hydrocarbons" or "Cn", wherein "n" is a positive integer, means hydrocarbons having "n" number of carbon atoms. The term "Cn+" is meant to describe a mixture of hydrocarbons having "n" or more carbon atoms. The term "Cn−" is meant to describe to a mixture of hydrocarbons having "n" or less carbon atoms.

The term "octane number" refers to the percentage of iso-octane in a mixture of iso-octane and n-heptane that would have the same knock resistance as the presently tested fuel, according to ASTM D2699 and D2700. Octane numbers typically range from 0 to 100, with higher values indicating better fuel performance. Octane numbers are unitless.

The term "Research Octane Number" (RON) refers to the octane number obtained by testing at lower engine speed and temperature, typically about 600 rpm, according to ASTM D2699.

The term "Motor Octane Number" (MON) refers to the octane number obtained by testing at higher engine speed and temperature, typically about 900 rpm according to ASTM D2700. Given that engine inefficiency inherently increases as temperature increases, RON is typically higher than MON.

"Anti-knock index" is defined by the arithmetic average of the two octane numbers: (RON+MON)/2.

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

Isobutane Feed

The isobutane feed stream to alkylation unit generally comprises at least 50 wt. % isobutane (e.g., 50 wt. % to 99 wt. % isobutane, or 50 wt. % to 95 wt. % isobutane, or 55 wt. % to 90 wt. % isobutane, or at least 80 wt. % isobutane, or 80 wt. % to 98 wt. % isobutane, or 90 wt. % to 97 wt. % isobutane), with at least 90 wt. % (e.g., at least 99 wt. %) of the remainder comprising n-butane. The isobutane feed may be substantially free of one or more of (i) butenes, including isobutene, (ii) C5+ hydrocarbon, and (iii) C3-hydrocarbon.

In this context, the term "substantially free" means the isobutane feed comprises less than or equal to 1.0 wt. % of the designated compounds (e.g., less than or equal to 0.1 wt. %, or less than or equal to 0.01 wt. %, or less than or equal to 0.001 wt. %).

Ethylene Feed Stream

Ethylene feed streams useful herein may include dilute ethylene streams, containing up to 50 wt. % ethylene, for example. In some aspects, the ethylene feed stream may include a low purity ethylene feed, including 60 wt. % to 95 wt. % ethylene. In other aspects, the ethylene feed stream may include high purity ethylene (95 wt. % to 99+ wt. % ethylene).

The dilute ethylene stream derived from any number of refinery streams. The dilute ethylene stream may be an off-gas from a refinery unit selected from an ethylene cracker, a fluid catalytic cracker, a coker, a naphtha cracker, a Fischer-Tropsch synthesis unit, an ethylene polymerization unit, or a pyrolysis unit.

The dilute ethylene stream may contain from 0.1 wt. % to 50 wt. % ethylene, such as from 5 wt. %, 10 wt. %, or 15 wt. % to 30 wt. %, 40 wt. %, or 50 wt. % ethylene. A suitable dilute ethylene stream may comprise from 5 wt. % to 50 wt. % ethylene. The balance of the dilute ethylene stream may include hydrogen, nitrogen, methane, ethane, propylene, and/or propane. For example, a typical FCC off-gas may include 50 wt. % to 70 wt. % methane and hydrogen, with the balance being about equal parts ethane and ethylene, as well as a minor amount of C3+ compounds.

In some aspects, the ethylene feed stream may be a polymer-grade ethylene stream, which may have at least 98 wt. %, or at least 99 wt. %, or at least 99.5 wt. %, or at least 99.8 wt. % ethylene.

Ionic Liquid

The ionic liquid comprises an organic cation and an anion. The organic cation is generally a nitrogen-based cation, a phosphorus-based cation, or a combination thereof. Representative organic cations include ammonium, pyrrolidinium, pyridinium, imidazolium, and phosphonium cations.

Examples of ammonium cations include tetraalkylammonium cations, such as tri(C1-C6 alkyl)-(C2-C10 alkyl)ammonium cations. Representative ammonium cations include trimethyl-n-propylammonium, n-butyl-trimethylammonium, n-hexyl-trimethylammonium, triethyl-methylammonium, tetraethylammonium, n-butyl-triethylammonium, and tetra-n-butylammonium.

Examples of pyrrolidinium cations include N-alkylpyrrolidinium cations, such as N—(C2-C6 alkyl)pyrrolidinium cations, and N,N-dialkylpyrrolidinium cations, such as N—(C1-C3 alkyl)-N—(C2-C6 alkyl)pyrrolidinium cations. Representative pyrrolidinium cations include N-propylpyrrolidinium, N-butylpyrrolidinium, N-methyl-N-propylpyrrolidinium and N-butyl-N-methylpyrrolidinium.

Examples of imidazolium cations include 1,3-dialkylimidazolium cations, such as 1-(C2-C10 alkyl)-3-(C1-C3 alkyl) imidazolium cations. Representative imidazolium cations include 1-ethyl-3-methylimidazolium, 1-n-butyl-3-methylimidazolium, 1-n-hexyl-3-methylimidazolium, and 1-n-octyl-3-methylimidazolium.

Examples of pyridinium cations include N-alkylpyridinium cations, such as N—(C2-C6 alkyl)pyridinium cations, and N-alkyl-alkylpyridinium cations, such as N—(C2-C6 alkyl)-(C1-C3 alkyl)pyridinium cations. Representative pyridinium cations include N-ethylpyridinium, N-butylpyridinium, N-propyl-4-methylpyridinium and N-butyl-4-methylpyridinium.

Examples of phosphonium cations include tetraalkylphosphonium cations, such as tri(C1-C10 alkyl)-(C2-C20 alkyl) phosphonium cations. Representative phosphonium cations include triethyl-pentylphosphonium, tetrabutylphosphonium, and trihexyl-tetradecylphosphonium.

The anion of the ionic liquid comprises a halometallate. Halometallate anions may contain a metal selected from Al, Ga, In, Mn, Fe, Co, Ni, Cu, Zn, or combinations thereof, and a halide selected from F, Cl, Br, I, or combinations thereof. In some aspects, the anion of the ionic liquid comprises a haloaluminate. In some aspects, the anion of the ionic liquid comprises a chloroaluminate. For catalytic applications requiring Lewis acidity (such as alkylation), the ratio of moles of halide to moles of metal in the halometallate anion is less than 4. The anion may be formally an anion or it may be an anion associated with a metal halide. For instance, the anion may be $AlCl_4^-$ or $Al_2Cl_7^-$ associated with $AlCl_3$. In some aspects, the anion may be $GaCl_4^-$ or $Ga_2Cl_7^-$ or $Ga_3Cl_{10}^-$ associated with $GaCl_3$ The ionic liquid catalyst can include a co-catalyst (or catalyst promoter) to enhance the activity of the ionic liquid catalyst by boosting its overall acidity. The co-catalyst may be a Brønsted acid and/or a Brønsted acid precursor. The co-catalyst is present in an amount of 0.05 mol to 1 mol of co-catalyst per mol of ionic liquid, or 0.05 mol to 0.7 mol, or 0.05 mol to 0.5 mol, or 0.1 mol to 0.7 mol, or 0.1 mol to 0.5 mol. Suitable Brønsted acids include HCl, HBr, HI, and combinations thereof. In some aspects, the co-catalyst can be generated in situ from appropriate Brønsted acid precursors. Suitable Brønsted acid precursors include chloroalkanes such as 1-chloropropane, 2-chloropropane, 1-chlorobutane, 2-chlorobutane, 1-chloro-2-methylpropane, 2-chloro-2-methylpropane, and other chloroalkanes, preferably secondary or tertiary chloroalkanes, or combinations thereof. In some aspects, the Brønsted acid precursor is a chloroalkane having more than one chloride atom per molecule such as dichloromethane, chloroform, carbon tetrachloride, tetrachloroethylene, tetrachloropropene, or combinations thereof.

Alkylation

Typical alkylation reaction conditions include a minimum temperature of 30° C., or 35° C., or 40° C., or 45° C., or 50° C., or 55° C., or 60° C.; additionally or alternatively, a maximum temperature of 100° C., or 95° C., or 90° C., or 85° C., or 80° C., or 75° C., or 70° C. Generally, the temperature can be in a range from any minimum temperature disclosed herein to any maximum temperature disclosed herein. It is preferred to have the ionic liquid that maintains its liquid state through the operating temperature range.

The alkylation reaction can be conducted at a pressure of from 100 psig to 1000 psig (689 kPa to 6895 kPa), such as 300 psig to 700 psig (2068 kPa to 4826 kPa), or 350 psig to 500 psig (2413 kPa to 3447 kPa). Preferably, the reactants are maintained in a liquid state at the operating pressure.

The residence time of the reactants in the reaction zone is in a range of from a few seconds to several hours (e.g., 30 seconds to 1 hour, or 2 minutes to 30 minutes, or 2 minutes to 10 minutes, or 5 minutes to 1 hour, or 5 minutes to 30 minutes, 5 minutes to 10 minutes).

The volume of ionic liquid in the reactor may be in a range of from 1 vol. % to 75 vol. % of the total volume of material in the reactor (ionic liquid and hydrocarbons), or 1 vol. % to 70 vol. %, or 1 vol. % to 65 vol. %, or 1 vol. % to 60 vol. %, or 1 vol. % to 55 vol. %, or 1 vol. % to 50 vol. %, or 1 vol. % to 45 vol. %, or 1 vol. % to 40 vol. %, or 1 vol. % to 35 vol. %, or 1 vol. % to 30 vol. %, or 1 vol. % to 25 vol. %, or 1 vol. % to 20 vol. %, or 1 vol. % to 15 vol. %, or 1 vol. % to 10 vol. %, or 1 vol. % to 5 vol. %. In aspects where the volume of ionic liquid in the reactor is less than 50 vol. %, the reaction mixture comprises a dispersed ionic liquid phase and a continuous hydrocarbon phase. In aspects where the volume of ionic liquid in the reactor is greater than 50 vol. %, the reaction mixture comprises a dispersed hydrocarbon phase and a continuous ionic liquid phase.

Due to the low solubility of hydrocarbons in ionic liquids, isoparaffin-olefin alkylation, like most reactions in ionic liquids, is generally biphasic. The catalytic alkylation reaction is generally carried out in a mixed phase liquid-liquid system. The system can be a batch system, a semi-batch system, or a continuous system as is usual for aliphatic alkylation. Vigorous mixing is desirable to ensure good contact between the reactants and the catalyst.

The isoparaffin and olefin can be introduced in the reactor separately or as a mixture, in one or multiple locations. The molar ratio of isoparaffin to olefin is generally 20:1 or less, or 15:1 or less, or 10:1 or less, or in a range of 2:1 to 20:1, or in a range of 2:1 to 15:1, or in a range of 2:1 to 10:1, or in a range of 2:1 to 8:1, or in a range of 2:1 to 6:1, or in a range of 2:1 to 4:1, or in a range of 5:1 to 20:1, or in a range of 5:1 to 15:1, or in a range of 5:1 to 10:1.

In a semi-batch system, the catalyst, optional co-catalyst, and at least a portion of the isoparaffin are introduced with no olefin present, followed by the olefin or a mixture of isoparaffin and olefin. In a semi-batch system, the olefin is added gradually over a period of time. The catalyst is measured in the reactor with respect to the amount of total olefins added over the course of the reaction, with a catalyst to olefin weight ratio in a range of from 0.1:1 to 10:1 (e.g., 0.2:1 to 5:1, or 0.5:1 to 2.5:1).

In a continuous system, the ionic liquid catalyst, the isoparaffin, the olefin, and optionally the co-catalyst are each added continuously. Catalyst, optional co-catalyst, unreacted isoparaffin, and unreacted olefin are each removed continuously from the reaction zone along with alkylate product. The catalyst, co-catalyst, unreacted isoparaffin, and/or unreacted olefin may be recycled. The olefin may be added to one or more locations in the reaction zone. It is preferable to add the olefin to multiple locations in the reaction zone. Adding olefin in multiple locations or spreading the olefin addition over a longer period of time, results in the isoparaffin to olefin ratio measured in a specific location at a specific point in time to be higher. The isoparaffin to olefin ratio is defined as the cumulative amount of isoparaffin divided by the cumulative amount of olefin added across the entire reaction zone.

Heat generated by the alkylation reaction can be removed using any of the methods known to those of skill in the art.

Conjunct polymer forms as a by-product of the alkylation reaction. Conjunct polymers are typically highly conjugated, olefinic, highly cyclic hydrocarbons and have a strong affinity for the ionic liquid catalyst. The ionic liquid catalyst loses its effectiveness over time as the amount of conjunct polymer increases. Over time, the ionic liquid catalyst must then either be replaced or regenerated. Generally, only as much ionic liquid catalyst is regenerated as is necessary to maintain a desired level of catalyst activity. Generally, the alkylation process is operated at conditions sufficient to maintain a desired level of conjunct polymer in the ionic liquid. The amount of conjunct polymer in the ionic liquid during alkylation may be maintained at 10 wt. % or less (e.g., 9 wt. % or less, or 8 wt. % or less, or 7 wt. % or less, or 6 wt. % or less, or 5 wt. % or less, or 4 wt. % or less, or 3 wt. % or less, or 2 wt. % or less, 1 wt. % or less). For example, the amount of conjunct polymer in the spent ionic liquid may be maintained in a range of from 0.5 to 10 wt. %, or 1 to 5 wt. %, or 2 to 4 wt. %. An amount of conjunct polymer in an ionic liquid phase can be measured using infrared spectroscopy, such as disclosed in U.S. Pat. No. 9,290,702.

At the reactor outlet, the hydrocarbon phase is separated from the ionic liquid phase by gravity settling based on density differences, or by other separation techniques known to those skilled in the art. Then the hydrocarbons are separated by distillation, and the starting isoparaffin which has not been converted is recycled to the reactor. The catalyst is typically recycled to the reactor as well.

Typical alkylation conditions may include a temperature of from 30° C. to 100° C., a pressure of from 300 psig to 700 psig (2068 kPa to 4826 kPa), an isoparaffin to olefin molar ratio of from 2:1 to 20:1, a residence time of from 5 minutes to 1 hour, an ionic liquid volume in the reactor of from 1 vol % to 70 vol %.

The conversion of ethylene is typically at least 95% (e.g., at least 96%, or at least 97%, or at least 98%, or at least 99%). The percent ethylene conversion is defined as: (the amount of ethylene added to the reactor minus the amount of ethylene remaining after the reaction (or at the reactor outlet)) divided by the total amount of ethylene added to the reactor times 100. In a continuous process, ethylene conversion is defined as: (the amount of ethylene added to the reactor minus the total flow of ethylene out of the reactor) divided by the total flow of ethylene into the reactor.

FIG. 1 illustrates one embodiment of an alkylation process according to the present disclosure. An isobutane feed stream 105, an ethylene feed stream 110, and an ionic liquid catalyst composition stream 115, optional co-catalyst, are fed to an alkylation zone 120. The isobutane and the ethylene react in the presence of the ionic liquid catalyst composition to form alkylate.

The effluent 125 from the alkylation zone 120 contains alkylate, unreacted isobutane, the ionic liquid catalyst, and possibly unreacted ethylene. The effluent 125 is sent to a separation zone 130 where it is separated into a hydrocarbon stream 135 comprising the alkylate and unreacted isobutane (and any unreacted ethylene) and an ionic liquid recycle stream 140. Suitable separation zones include gravity settlers, coalescers, filtration zones comprising sand or carbon, adsorption zones, scrubbing zones, or combinations thereof.

The hydrocarbon stream 135 is sent to a hydrocarbon separation zone 145 where it is separated into an alkylate stream 150 and an isobutane and co-catalyst recycle stream 155. The alkylate stream 150 can be recovered and further treated as needed. The isobutane and co-catalyst recycle stream 155 can be recycled to the alkylation zone 120, if desired. Suitable hydrocarbon separation zones include distillation or vaporization.

The ionic liquid recycle stream 140 which typically contains some amount of conjunct polymer is also recovered from the separation zone 130 and can be recycled to the alkylation zone 120, if desired. In some embodiments, at least a portion 160 of the ionic liquid recycle stream 140 can be sent to a regeneration zone 165 to remove at least some of the conjunct polymer from the ionic liquid recycle stream to provide a regenerated ionic liquid. The regenerated ionic liquid recycle stream 170 can be recycled to the alkylation zone 120.

Alkylate

In some aspects, the process can be used to upgrade low value C4 hydrocarbons to higher value alkylates. To that extent, one specific aspect is the alkylation of isobutane with ethylene to generate C6 compounds. Preferred products include isomers of dimethylbutane (DMB), namely, 2,3-dimethylbutane and 2,2-dimethylbutane. Other C6 isomers are also produced. One set competing isomers are methylpentanes (MP), namely 2-methylpentane and 3-methylpentane. The quality of the alkylate can be measured in the ratio of DMB to MP, with a high ratio desired (e.g., at least 7:1 or more, or at least 10:1 or more, or at least 12:1 or more, or at least 15:1 or more, or at least 20:1 or more).

In some aspects, the alkylation reaction can have a selectivity for C6 of at least 65% or more, or at least 70% or more, or at least 75% or more. Selectivity for C6 is defined here as the total weight of products containing exactly six carbon atoms divided by the total weight of products containing five or more carbon atoms. In some aspects, the alkylate can have a mole ratio of dimethylbutane to methylpentane of at least 4:1 or more, or 7:1 or more, or at least 10:1 or more, or at least 12:1 or more, or at least 15:1 or more, or 20:1 or more, or 25:1 or more, or 30:1 or more, or 35:1 or more.

The alkylate may contain C8 paraffins. Preferred products include isomers of trimethylpentane (TMP), namely 2,2,3-trimethylpentane, 2,2,4-trimethylpentane, 2,3,3-trimethylpentane, and 2,3,4-trimethylpentane. Other C8 isomers are also produced. One set of competing isomers are dimethylhexanes (DMH), namely 2,2-dimethylhexane, 2,3-dimethylhexane, 2,4-dimethylhexane, 2,5-dimethylhexane, 3,3-dimethylhexane, and 3,4-dimethylhexane. The quality of the product stream can be measured in the ratio of total TMP to total DMH, with a higher ratio desired (e.g., of greater than 2:1, or greater than 3:1). C8 isomers may be present in an amount of 30 wt. % or less (e.g., 1 wt. % to 30 wt. %, or 5 wt. % to 15 wt. %) of the alkylate.

The alkylate may contain C9+ paraffins. The C9+ paraffins may be present in an amount of less than 20 wt. % (e.g., less than 10 wt. %) of the alkylate.

In some embodiments, the alkylate has a research octane number (RON) of 93 or more (e.g., 94 or more, 95 or more, 96 or more, 97 or more, 98 or more, 99, or 100 or more).

EXAMPLES

The following illustrative examples are intended to be non-limiting.

Example 1

Ionic Liquid Catalyst

The ionic liquid catalyst used herein was N-butylpyridinium chloroaluminate, which was prepared according to U.S. Pat. No. 7,495,144. Table 1 shows the chemical composition of the catalyst.

TABLE 1

Composition of the N-Butylpyridinium Chloroaluminate Ionic Liquid Catalyst

| Element | Weight % |
|---|---|
| Al | 12.4 |
| Cl | 56.5 |
| C | 24.6 |
| H | 3.2 |
| N | 3.3 |

Examples 2-5

Alkylation of Isobutane with Ethylene Using N-Butylpyridinium Chloroaluminate Ionic Liquid Catalyst To a 100-1000 mL Parr autoclave reactor, isoparaffin feed controlled by a Quizix pump, olefin controlled by a Bronkhorst flow controller, HCl co-catalyst controlled by a Bronkhorst flow controller, and ionic liquid catalyst controlled by a LEWA pump were continuously fed. Both the hydrocarbon feed and HCl co-catalyst were fed to the top of the reactor while the ionic liquid was fed to the bottom of the reactor. The reactor contents were heated to a target temperature under a target pressure with overhead stirring. The target process conditions are shown in Examples. The reactor effluent was taken from the top of the reactor. The reactor effluent was separated in a downstream separator into a separate product phase and an ionic liquid catalyst phase. The product was analyzed by gas chromatography.

Figure 2:
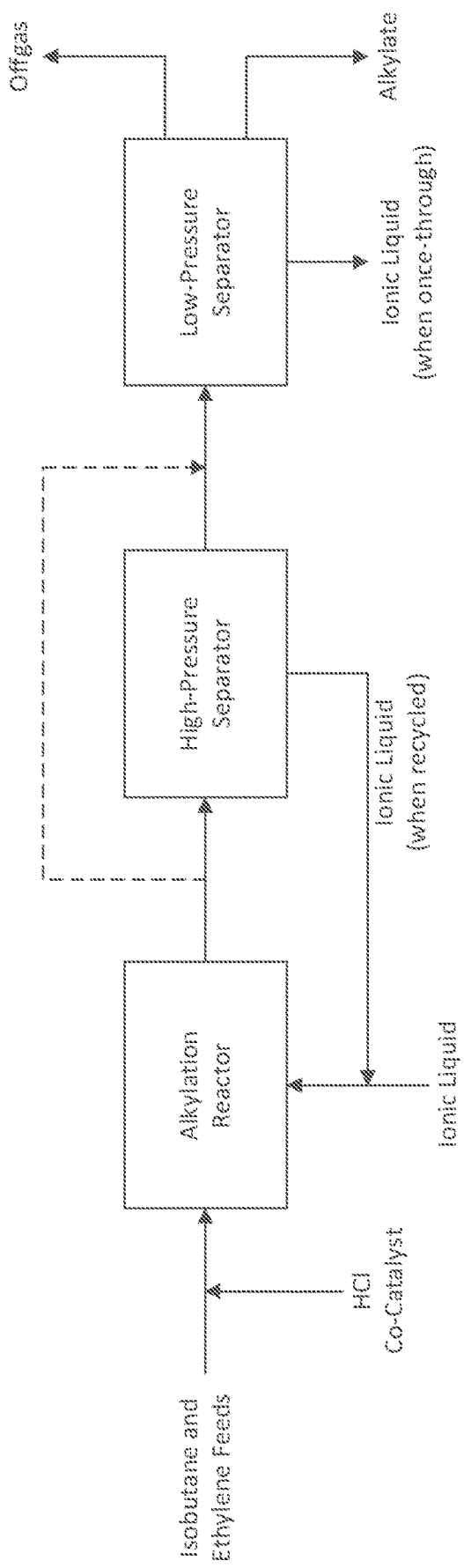
FIG. 2 is an illustration of one embodiment of an alkylation process of the present disclosure.

Isobutane was obtained from a refinery FCC stream. The ethylene feed was Ultra-High Purity (UHP) grade ethylene purchased from Airgas. Table 2 shows the chemical composition of the isobutane and ethylene feeds. FIG. 2 shows a simplified process flow diagram for alkylation of isobutane with ethylene.

TABLE 2

Composition of the Isobutane and Ethylene Feeds

| Isobutane Feed | Weight % |
|---|---|
| Propane | 6.3 |
| Isobutane | 79.9 |
| n-Butane | 12.4 |
| Isopentane | 1.4 |
| Ethylene Feed | |
| Ethylene | 99.9 |

Table 3 shows conditions and results for isobutane alkylation with ethylene.

TABLE 3

Conditions and Results for Isobutane Alkylation with Ethylene

| | Ex. 2 | Ex. 3 | Ex. 4 | Ex. 5 |
|---|---|---|---|---|
| Alkylation Conditions | | | | |
| Temperature [° F.] | 140 | 120 | 100 | 90 |
| Pressure [psig] | 400 | 400 | 400 | 180 |
| Isoparaffin/Olefin molar ratio | 8 | 8 | 8 | 8 |
| Ionic Liquid Content [vol. %] | 10 | 10 | 10 | 10 |
| Residence Time [min] | 8 | 8 | 10 | 6 |
| Olefin/HCl molar ratio | 30 | 30 | 25 | 47 |
| Ethylene Conversion [%] | 98.0 | 96.0 | 99.7 | 38.0 |
| Alkylate Properties | | | | |
| Cn Selectivity [%] | | | | |
| C5 | 0.9 | 2.9 | 7.0 | 2.4 |
| C6 | 87.2 | 85.1 | 71.4 | 55.9 |
| C7 | 1.1 | 1.4 | 4.2 | 3.0 |
| C8 | 8.1 | 6.9 | 10.0 | 26.3 |
| C9 | 0.3 | 0.8 | 2.1 | 3.0 |
| C10 | 1.0 | 1.3 | 2.6 | 4.7 |
| C11 | 0.7 | 0.6 | 1.7 | 3.5 |
| C12+ | 0.8 | 1.0 | 1.0 | 1.2 |
| C6 Isomer | | | | |
| Relative Distribution [%] | | | | |
| 2,2-Dimethylbutane | 0 | 1 | 2 | 0.3 |

TABLE 3-continued

Conditions and Results for Isobutane Alkylation with Ethylene

|  | Ex. 2 | Ex. 3 | Ex. 4 | Ex. 5 |
|---|---|---|---|---|
| 2,3-Dimethylbutane | 97 | 96 | 78 | 97 |
| 2-Methylpentane | 2 | 3 | 12 | 2.8 |
| 3-Methylpentane | 1 | 1 | 5 | 0 |
| Dimethylbutane/Methylpentane molar ratio | 32.3 | 24.3 | 4.7 | 34.8 |
| C8 Isomer Relative Distribution [%] | | | | |
| Trimethylpentanes | 70 | 68 | 53 | 47 |
| Dimethylhexanes | 21 | 19 | 34 | 50 |
| Methylheptanes | 8 | 11 | 12 | 3 |
| Octane Number | | | | |
| RON | 101.0 | 100.4 | 94.3 | 96.8 |
| MON | 93.8 | 93.4 | 90.4 | 91.0 |
| SIMDIST (ASTM D2887) [° F.] | | | | |
| T50 | 136 | 138 | 137 | 157 |
| T90 | 192 | 193 | 227 | 285 |
| T99 | 295 | 293 | 378 | 418 |
| FBP (T99.5) | 356 | 363 | 423 | 441 |

The results show that alkylate produced from direct conversion of isobutane with ethylene by highly active ionic liquid catalyst contained predominantly C6 and C8 paraffins. Product selectivity to C6 alkylate (reaction product of 1 mole of ethylene and 1 mole of isobutane) and C8 alkylate (reaction product of 2 mole of ethylene and 1 mole of isobutane) can be controlled. Different amounts of C6 and C8 can be produced depending on process conditions selected.

The C8 isomer distribution can vary depending upon the conditions selected. C8 isomers can be predominately high-octane number trimethylpentanes or predominately low-octane number dimethylhexanes. At relatively lower reaction temperatures and lower reaction pressure, the overall C6 selectivity significantly decreased and C8 selectivity significantly increased. Among C8 isomers, low-octane number dimethylhexanes significantly increased while high-octane trimethylpentanes significantly decreased, resulting in a poor quality alkylate.

Under carefully selected and controlled process conditions (Examples 2-4), high conversion of ethylene was achieved (>96%). When the reaction temperature and pressure were not sufficiently high, however, the conversion of ethylene was very low at 38%, and a substantial amount of ethylene was found unreacted (Example 5). These results were surprising compared with the conventional C3 and C4 olefin alkylation processes where nearly 100% conversion of olefins is observed with an ionic liquid catalyst. This indicates that ethylene has very low reactivity compared with C3 and C4 olefins.

As the reactor temperature was lowered from 140° F. to 100° F. (Examples 2-4), a decline in the RON octane number from 101 to 94 was observed. These results were surprising in comparison to conventional C3 and C4 olefin alkylation processes where lower temperatures provide alkylate with better RON octane numbers. Furthermore, it was surprising to discover that the C8 isomer distribution, as a function of temperature, for ethylene alkylation was the opposite of what is observed for conventional C3 and C4 olefin alkylation. At lower reaction temperatures, dimethylhexanes significantly increased while trimethylpentanes significantly decreased, resulting in poorer alkylate quality (lower octanes) for ethylene alkylation. For C3 and C4 olefin alkylation, lower reaction temperatures increased trimethylpentanes significantly, the opposite trend (see Examples 8-9).

Example 6 (Comparative)

Alkylation of Isopentane with Ethylene Using N-Butylpyridinium Chloroaluminate Ionic Liquid Catalyst Alkylation of isopentane with ethylene using N-butylpyridinium chloroaluminate ionic liquid catalyst was carried in accordance with U.S. Pat. No. 7,432,408.

Conditions and results for isopentane alkylation with ethylene are shown in Table 5 below.

Example 7 (Comparative)

Alkylation of Isobutane with C3/C4 Olefins Using N-Butylpyridinium Chloroaluminate Ionic Liquid Catalyst For Examples 7-9, refinery isobutane containing 85% isobutane and 15% n-butane was used after drying with 13× molecular sieve.

A refinery olefin stream containing a mixture of C3 and C4 olefins (C3/C4 olefins) was dried with 13× molecular sieve and isomerized with a Pd/Al$_2$O$_3$ catalyst at 150° F., 250 psig in the presence of hydrogen to produce an isomerized C3/C4 olefin feed with the composition shown in Table 4.

TABLE 4

Composition of C3/C4 Olefin Feed

| Component | Mol. % |
|---|---|
| Propane | 13.3 |
| Propylene | 25.4 |
| 1-Butene | 2.3 |
| 2-Butene | 16.2 |
| Isobutylene | 6.7 |
| n-Butane | 12.4 |
| Isobutane | 22.2 |
| C5+ | 1.6 |

Evaluation of C3/C4 olefin alkylation with isobutane was performed in a continuously stirred tank reactor. An 8:1 molar mixture of isobutane and olefin was fed to the reactor with vigorous stirring. Ionic liquid catalyst (N-butylpyridinium chloroaluminate) was fed to the reactor via a second inlet port targeting to occupy 6 vol. % in the reactor. A small amount of n-butyl chloride was added to produce anhydrous HCl gas. The average residence time (combined volume of feeds and catalyst) was about 12 minutes. The outlet pressure was maintained at 200 psig and the reactor temperature was maintained at 95° F. (35° C.) using external cooling.

The reactor effluent was separated with a coalescing separator into a hydrocarbon phase and an ionic liquid catalyst phase. The hydrocarbon stream was further separated into multiple streams with three distillation columns: a gas stream containing C3− hydrocarbons, an n-C4 stream, an i-C4 stream and an alkylate stream. The ionic liquid catalyst was recycled back to the alkylation reactor for repeated use. To maintain the activity of the ionic liquid catalyst, a fraction of used ionic liquid catalyst was sent to a hydrogenation reactor for a reduction of the amount of conjunct polymer in the ionic liquid catalyst. The amount of conjunct polymer in the ionic liquid catalyst was maintained in a range of from 2-6% to obtain good quality alkylate gasoline. The amount of conjunct polymer in the ionic liquid catalyst was determined by Fourier transform infrared (FT-IR) spectroscopy in accordance with U.S. Pat. No. 9,290,702.

Table 5 shows conditions and results for isobutane alkylation with C3/C4 olefins.

Examples 8-9 (Comparative)

Alkylation of Isobutane with C4 Olefins Using N-Butylpyridinium Chloroaluminate Ionic Liquid Catalyst Alkylation was carried out as described in Examples 2-5 except that the olefin was a mixture of C4 olefins.

Table 5 shows conditions and results for isobutane alkylation with C4 olefins.

TABLE 5

Conditions and Results for Isoparaffin-Olefin Alkylation

| | Ex. 2 | Ex. 6 | Ex. 7 | Ex. 8 | Ex. 9 |
|---|---|---|---|---|---|
| Olefin Feed | C2 | C2 | C3/C4 | C4 | C4 |
| Isoparaffin Feed | i-C4 | i-C5 | i-C4 | i-C4 | i-C4 |
| Alkylation Conditions | | | | | |
| Temperature [° F.] | 140 | 122 | 95 | 95 | 50 |
| Pressure [psig] | 400 | 300 | 200 | 150 | 150 |
| Isoparaffin/Olefin mole ratio | 8 | 4 | 8 | 8 | 8 |
| Ionic Liquid Content [vol. %] | 10 | 15 | 6 | 4 | 5 |
| Residence Time [min] | 8 | 40 | 12 | 4 | 5 |
| Olefin/HCl mole ratio | 30 | — | 60 | 49 | 40 |
| Olefin Conversion [%] | 98.0 | 95.0 | 100 | 100 | 100 |
| Alkylate Properties | | | | | |
| Cn Selectivity [%] | | | | | |
| C5 | 0.9 | 4.1$^{(a)}$ | | 4.5 | 6.0 |
| C6 | 87.2 | 8.0 | | 6.3 | 6.9 |
| C7 | 1.1 | 63.3 | | 7.0 | 5.2 |
| C8 | 8.1 | 9.1 | | 66.4 | 65.0 |
| C9 | 0.3 | 7.1 | | 9.2 | 8.3 |
| C10 | 1.0 | 4.2 | | 3.1 | 4.6 |
| C11 | 0.7 | 4.3$^{(b)}$ | | 3.2 | 3.1 |
| C12 | 0.8 | — | | 0.2 | 0.9 |
| C8 Isomer Relative Distribution [%] | | | | | |
| Trimethylpentanes | 70 | | | 81 | 87 |
| Dimethylhexanes | 21 | | | 17 | 9 |
| Octane Number | | | | | |
| RON | 101 | 87 | 89 | 95 | 97 |
| MON | 93.8 | 84 | 86 | 92.2 | 93.4 |
| SIMDIST (ASTM D2887) [° F.] | | | | | |
| FBP (99.5) | 356 | | | 376 | 378 |

$^{(a)}$C5−.
$^{(b)}$C11+.

The results presented in Tables 3 and 5 show that ethylene alkylation at relatively higher reaction temperatures (e.g., 100° F. and above) provided very high olefin conversion (≥96.0%) and generated alkylate with high octane numbers (Examples 2 and 3 vs. 4 and 5). This result is contrary to conventional C4 olefin alkylation, where a relatively lower temperature (e.g., less than 100° F.) provided 100% conversion and high octane numbers (Examples 8 and 9). For ethylene alkylation, the dimethylhexane content in C8 isomers significantly increased as the reaction temperature is lowered (Table 3). For C3 and C4 olefin alkylation, lower reaction temperature increases the trimethylpentanes significantly, the opposite trend (Examples 8 vs. 9). Again, this result is contrary to conventional C4 olefin alkylation, Example 10

Composition of Alkylate Gasoline Made by Ethylene Alkylation with Isobutane

It was discovered that, depending on the process conditions, the C8 isomer composition varied significantly. C8 isomers can be predominately trimethylpentanes (100-110 RON) or predominately dimethylhexanes (56-76 RON). At carefully selected process conditions, C8 isomer composition was comprised of over 70% trimethylpentanes.

It was discovered that, at carefully selected process conditions, C6 composition was comprised of over 95% 2,3-dimethylbutane (103.5 RON).

It was very surprising to discover that at lower reaction temperature of 90° F. and lower reaction pressure of 180 psig, overall C6 selectivity significantly decreased and C8 selectivity significantly increased. Also, among C8 isomers, dimethylhexanes significantly increased, and trimethylpentanes significantly decreased, resulting in poor alkylate quality (lower octanes) clearly indicating that process conditions for ethylene alkylation must be carefully selected and controlled.

The study above showed that a new alkylate composition can be obtained by ethylene alkylation with isobutane with an ionic liquid catalyst at the preferred process conditions. The composition of the alkylate of the present disclosure can be summarized as follows in Table 6.

TABLE 6

Gasoline Alkylate Composition

| Feature | Composition Range |
|---|---|
| Carbon Number Range | C5-C14 |
| C6 [wt. %] | 70-90 |
| C8 [wt. %] | 6-30 |
| C9+ [wt. %] | <10 |
| 2,3-Dimethylbutane/Total C6 [%] | 75-99 |
| Trimethylpentanes/Total C8 [%] | 50-80 |

The invention claimed is:

1. An alkylation process comprising:
   passing an isobutane feed and an ethylene feed to an alkylation reactor, wherein the alkylation reactor contains an ionic liquid catalyst, the ionic liquid comprising an organic cation and a halometallate anion, for reacting the isobutane and ethylene to generate an alkylate having a research octane number (RON) of 93 or more;
   wherein the alkylation reactor is operated at reaction conditions including a temperature of from 30° C. to 100° C., a pressure of from 300 psig to 700 psig (2068 kPa to 4826 kPa), an overall isobutane to ethylene molar ratio from 2 to 20, and a residence time of from 5 minutes to 1 hour.

2. The process of claim 1, wherein the ethylene feed is a dilute ethylene feed stream, a polymer-grade ethylene feed stream, or a combination thereof.

3. The process of claim 2, wherein the polymer-grade ethylene feed stream comprises at least 98 wt. % ethylene.

4. The process of claim 1, wherein the organic cation of the ionic liquid comprises an ammonium cation, a pyrrolidinium cation, a pyridinium cation, an imidazolium, a phosphonium cation, or a combination thereof.

5. The process of claim 1, wherein the halometallate anion comprises a metal selected from Al, Ga, In, Mn, Fe, Co, Ni, Cu, Zn, or a combination thereof, and a halide selected from F, Cl, Br, I, or a combination thereof.

6. The process of claim 1, wherein the halometellate anion is a haloaluminate anion.

7. The process of claim 1, wherein the ionic liquid is present in an amount of from 1 vol. % to 70 vol. % of a total volume of material in the alkylation reactor.

8. The process of claim 1, wherein the process has a selectivity for C6 of at least 70%, and the alkylate has a mole ratio of dimethylbutane to methylpentane of greater of at least 10.

9. The process of claim 1, wherein the alkylation reactor further comprises a co-catalyst.

10. The process of claim 9, wherein the co-catalyst comprises a Brønsted acid selected from the group consisting of HCl, HBr, HI, and mixtures thereof, or a Brønsted acid precursor.

11. The process of claim 1, wherein a conversion of the ethylene is at least 95%.

12. The process of claim 1, wherein the alkylate has a RON of 94 or more, or 95 or more, or 96 or more, or 97 or more, or 98 or more, or 99 or more, or 100 or more.

13. The process of claim 1, wherein the temperature is in a range of from 35° C. to 70° C.

14. The process of claim 1, wherein the pressure is in a range of from 350 psig to 500 psig (2413 kPa to 3447 kPa).

15. The alkylation process of claim 1 further comprising:
separating the alkylate and unreacted isobutane feed from the ionic liquid to form a hydrocarbon stream comprising the alkylate and the unreacted isobutane feed and an ionic liquid stream comprising the ionic liquid;
separating the hydrocarbon stream into an alkylate stream and an unreacted isobutane stream; and
recycling at least one of the unreacted isobutane stream and the ionic liquid stream.

16. The process of claim 15, further comprising:
regenerating at least a portion of the ionic liquid in the ionic liquid stream; and
recycling the regenerated ionic liquid catalyst to the alkylation reactor.

17. The alkylation process of claim 1, wherein the alkylation reactor is operated at a temperature of 100° F. (38° C.) or higher, and an alkylate having a research octane member (RON) of 100 or more is recovered.

18. The alkylation process of claim 1, wherein the alkylation reactor is operated at a temperature of 120° F. (49° C.) or higher.

* * * * *